United States Patent
Chen et al.

(10) Patent No.: US 8,673,862 B1
(45) Date of Patent: Mar. 18, 2014

(54) PEPTIDES AND USE THEREOF IN THE INHIBITION OF ANGIOTENSIN CONVERTING ENZYME

(75) Inventors: Yi-Hong Chen, Hsinchu (TW); Hsiang-Ling Lai, Hsinchu (TW); Shiao-Cheng Chuang, Hsinchu (TW); Chien-Ti Chang, Hsinchu (TW); Ming-Yu Hung, Hsinchu (TW); Yu-Hui Liu, Hsinchu (TW); Su-Er Liou, Hsinchu (TW); Fu-Ning Chien, Hsinchu (TW); Chu-Chin Chen, Hsinchu (TW)

(73) Assignee: Food Industry Research and Development Institute, Hsinchu (TW)

( * ) Notice: Subject to any disclaimer, the term of this patent is extended or adjusted under 35 U.S.C. 154(b) by 0 days.

(21) Appl. No.: 13/604,969

(22) Filed: Sep. 6, 2012

(51) Int. Cl.
 *A61K 38/08* (2006.01)
 *C07K 17/06* (2006.01)
 *A61K 38/55* (2006.01)

(52) U.S. Cl.
 CPC ............... *A61K 38/08* (2013.01); *C07K 17/06* (2013.01); *A61K 38/556* (2013.01)
 USPC ........ 514/21.8; 530/330; 514/16.2; 514/16.3; 514/16.4

(58) Field of Classification Search
 CPC ....... A61K 38/08; A61K 38/556; C07K 17/06
 See application file for complete search history.

(56) References Cited

U.S. PATENT DOCUMENTS

| | | | |
|---|---|---|---|
| 5,854,029 | A | 12/1998 | Yamamoto |
| 6,767,990 | B1 | 7/2004 | Chen et al. |
| 8,021,697 | B2 | 9/2011 | Kannar et al. |
| 8,063,017 | B2 | 11/2011 | Chen et al. |
| 2012/0107409 | A1 | 5/2012 | Huang et al. |

FOREIGN PATENT DOCUMENTS

| | | | |
|---|---|---|---|
| JP | 4264098 | A | 9/1992 |
| JP | 4299991 | A | 10/1992 |
| JP | 5331192 | A | 12/1993 |
| JP | 6298794 | A | 10/1994 |
| JP | 7289281 | A | 11/1995 |
| JP | 11-018776 | A * | 1/1999 |
| JP | 2002053595 | A | 2/2002 |

OTHER PUBLICATIONS

Overview of Hypertension-Merck Manual, pp. 1-18, accessed Mar. 7, 2013.*
Nephritic Syndrome-Merck Manual, pp. 1-13, accessed Mar. 7, 2013.*
Angina Pectoris-Merck Manual, pp. 1-14, accessed Mar. 7, 2013.*
Takayasu's Arteritis-Merck Manual, pp. 1-5, accessed Mar. 7, 2013.*
Chronic kidney disease—Merck Manual, pp. 1-8, accessed Mar. 7, 2013.*
Pereira et al, 2012 Brazilian Society of Rheumatology Consensus on the management of comorbidities in patients with rheumatoid arthritis, Rev Bras Reumatol, 2012, 52, pp. 474-495.*
JP11-018776A, machine translation used and enclosed, pp. 1-22, 1999.*
Maruyama, S. and Suzuki, H., A peptide inhibitor of angiotensin I converting enzyme in the tryptic hydrolysate of casein, Agric. Biol. Chem., 1982, 46: 1393-1394.
Maruyama, S. et al., Angiotensin I-converting enzyme inhibitor derived from an enzymatic hydrolysate of casein. II. Isolation and bradykinin-potentiating activity on the uterus and the ileum of rats, Agric. Biol. Chem., 1985; 49: 1405-1409.
Krysiak, R. et al, The effect of angiotensin-converting enzyme inhibitors on plasma adipokine levels in normotensive patients with coronary artery disease, Polish Journal of Endocrinology, 2010, 61: 280-286.
Yamamoto, N. et al., Antihypertensive effect of peptides derived from casein by an extracellular proteinase from *Lactobacillus helveticus* CP790, J. Dairy Sci., 1994, 77: 917-922.
Miyoshi et al., Structures and activity of angiotensin-converting enzyme inhibitors in an α-zein hydrolysate, Agric. Biol. Chem., 1991, 55: 1313-1318.
Yano, S. et al., Isolation from α-zein of thermolysin peptides with angiotensin I-converting enzyme inhibitory activity, Biosci. Biotech. Biochem., 1996, 60: 661-663.
Matsui, T. et al., Inhibition of angiotensin I-converting enzyme by *Bacillus licheniformis* alkaline protease hydrolyzates derived from sardine muscle, Biosci. Biotech. Biochem., 1993, 57: 922-925.
Matsufuji, H. et al,. Angiotensin I-converting enzyme inhibitory peptides in an alkaline protease hydrolyzate derived from sardine muscle, Biosci. Biotech. Biochem., 1994, 58: 2244-2245.
Matsumura, N. et al., Isolation and characterization of angiotensin I-converting enzyme inhibitory peptides derived from bonito bowels, Biosci. Biotech. Biochem., 1993, 57: 1743-1744.
Fujita, H. et al., Antihypertensive effect of thermolysin digest of dried bonito in spontaneously hypertensive rat, Clin. Exp. Pharmacol. Physiol. Suppl., 1995, 22: S304-S305.
Saito, Y. et al., Structure and activity of angiotensin I converting enzyme inhibitory peptides from sake and sake lees, Biosci. Biotechnol. Biochem., 1994, 58: 1767-1771.
Kinoshita, E. et al., Purification and identification of an angiotensin I-converting enzyme inhibitor from soy sauce, Biosci. Biotechnol. Biochem., 1993, 57: 1107-1110.
Okamoto, A. et al., Angiotensin I converting enzyme inhibitory activities of various fermented foods, Biosci. Biotechnol. Biochem., 1995, 59: 1147-1149.
Masuda, O. et al., Antihypertensive peptides are present in aorta after oral administration of sour milk containing these peptides to spontaneously hypertensive rats, J. Nutr., 1996, 126: 3063-3068.
Vermeirssen, V. et al., Optimisation and validation of an angiotensin-converting enzyme inhibition assay for the screening of bioactive peptides, J. Biochem. Biophys. Methods, 2002, 51: 75-87.

(Continued)

*Primary Examiner* — Julie Ha
*Assistant Examiner* — Li Ni Komatsu
(74) *Attorney, Agent, or Firm* — WPAT, P.C.; Anthony King; Kay Yang

(57) ABSTRACT

Peptides useful as angiotensin converting enzyme inhibitors are provided. Also provided are compositions comprising one or more of the peptides and methods for preventing, treating and/or diminishing one or more syndromes associated with angiotensin converting enzyme by using the peptides.

13 Claims, No Drawings

(56) References Cited

OTHER PUBLICATIONS

Pripp, A. H. et al., Quantitative structure-activity relationship modeling of ACE-inhibitory peptides derived from milk proteins, Eur. Food Res. Technol., 2004, 219: 579-583.

English Abstract of JP 7289281, 4299991, 2002053595, 6298794, 5331192, 4264098, Sep. 4, 2012.

Weisinger, Richard S. et al., Angiotensin converting enzyme inhibition lowers body weight and improves glucose tolerance in C57BL/6J mice maintained on a high fat diet. Physiol. Behavior. 98: 192-197. 2009.

Jones, Brynn H. et al., Angiotensin II increases lipogenesis in 3T3-L1 and human adipose cells. Endocrinol. 138: 1512-1519. 1997.

Massiera, Florence et al., Angiotensinogen-deficient mice exhibit impairment of diet-induced weight gain with alteration in adipose tissue development and increased locomotor activity. Endocrinol. 142: 5220-5225. 2001.

Saiki, Atsuhito et al., Circulating angiotensin II is associated with body fat accumulation and insulin resistance in obese subjects with type 2 diabetes mellitus. Metabol. Clin. Experiment. 58: 708-713. 2009.

Santos, Edson L. et al., Effect of angiotensin converting enzyme inhibitor enalapril on body weight and composition in young rats. Intl. Immunopharmacol. 8: 247-253. 2008.

Mogi, Masaki et al., Emerging concept of adipogenesis regulation by the rennin-angiotensin system. Hypertension 48: 1020-1022. 2006.

Santos, Edson Lucas et al., Long term treatment with ACE inhibitor enalapril decreases body weight gain and increases life span in rats. Biochem. Pharmacol. 78: 951-958. 2009.

Matsuzawa, Yuji et al,. The concept of metabolic syndrome: contribution of visceral fat accumulation and its molecular mechanism. J. Atheroscler. Thromb. 18: 629-639. Jul. 8, 2011.

Engeli, Stefan et al., Weight loss and the Renin-Angiotensin-Aldosterone System. Hypertension 45: 356-362. 2005.

Shi, Lijun et al., Angiotensin-converting enzymes and drug discovery in cardiovascular diseases. Drug Discovery Today 15: 332-341. May 2010.

Schiffrin, Ernesto L. et al., Chronic kidney disease: effects on the cardiovascular system. Circulation 116: 85-97. 2007.

Karalliedde, J. and Viberti, G., Evidence for renoprotection by blockade of the renin-angiotensin-aldosterone system in hypertension and diabetes. J. Human Hypertinsion 20: 239-253. 2006.

Basso, Nidia et al., Protective effect of long term angiotensin II inhibition. Am. J. Physiol. Heart Circ. Physiol. 293: H1351-H1358. Jun. 8, 2007.

Thatcher, Sean et al., The adipose rennin-angiotensin system: role in cardiovascular disease. Mol. Cell Endocrinol. Apr. 29, 2009. 302: 111-117.

Kloet, Annette D. De et al., the renin angiotensin system and the metabolic syndrome. Physiol. Behavior 100: 525-534. 2010.

\* cited by examiner

PEPTIDES AND USE THEREOF IN THE INHIBITION OF ANGIOTENSIN CONVERTING ENZYME

FIELD OF THE INVENTION

The present invention relates to novel peptides which are useful in the inhibition of angiotensin converting enzyme.

BACKGROUND OF THE INVENTION

Angiotensin converting enzyme (ACE) is present mainly in human vascular endothelial cells, lungs, kidneys and the brain. This enzyme may remove two amino acid residues (His-Leu) from the C-terminus of the inactivated angiotensin I to form an activated angiotensin II so as to cause contraction of blood vessels and increase blood pressure (Maruyama, S. and Suzuki, H., A peptide inhibitor of angiotensin I converting enzyme in the tryptic hydrolysate of casein, Agric. Biol. Chem., 1982, 46: 1393-1394). Maruyama, S. et al. (Angiotensin I-converting enzyme inhibitor derived from an enzymatic hydrolysate of casein. II. Isolation and bradykinin-potentiating activity on the uterus and the ileum of rats, Agric. Biol. Chem., 1985; 49: 1405-1409) found that ACE may inactivate bradykinin (having blood vessel dilating activity) so as to increase blood pressure. Therefore, the binding of an angiotensin converting enzyme inhibitor (ACEI) with ACE may reduce the formation of angiotensin II and the inactivation of bradykinin, so application of an ACEI may ameliorate hypertensive symptoms.

Krysiak, R. et al, (The effect of angiotensin-converting enzyme inhibitors on plasma adipokine levels in normotensive patients with coronary artery disease, Polish Journal of Endocrinology, 2010, 61: 280-286) discloses that ACE inhibitors are effective agents in patients with coronary artery disease (CAD), even if their blood pressure is within normal limits. U.S. Pat. No. 8,021,697 B2 discloses that ACE inhibitors can alter the distribution of body mass by decreasing overall percentage of fat and/or increasing the ratio of lean mass to fat mass. In other words, ACE inhibitors can reduce the amount of fat that is produced from consumed food.

In addition to chemically synthesized drugs, it has been found that many peptides having different lengths and amino acid residues can effectively inhibit ACE. The peptides having ACE inhibitory activity can be isolated from foods including, e.g., hydrolysates of animal or plant proteins, such as casein (Maruyama and Suzuki, 1982; Maruyama, S. and Suzuki, H., 1985; and Yamamoto, N. et al., Antihypertensive effect of peptides derived from casein by an extracellular proteinase from *Lactobacillus helveticus* CP790, J. Dairy Sci., 1994, 77: 917-922), corn protein (e.g., α-zein) (Miyoshi et al., Structures and activity of angiotensin-converting enzyme inhibitors in an α-zein hydrolysate, Agric. Biol. Chem., 1991, 55: 1313-1318 and Yano, S. et al., Isolation from α-zein of thermolysin peptides with angiotensin I-converting enzyme inhibitory activity, Biosci. Biotech. Biochem., 1996, 60: 661-663), sardine (Matsui, T. et al., Inhibition of angiotensin I-converting enzyme by *Bacillus licheniformis* alkaline protease hydrolyzates derived from sardine muscle, Biosci. Biotech. Biochem., 1993, 57: 922-925 and Matsufuji, H. Et al., Angiotensin I-converting enzyme inhibitory peptides in an alkaline protease hydrolyzate derived from sardine muscle, Biosci. Biotech. Biochem., 1994, 58: 2244-2245) and bonito (Matsumura, N. et al., Isolation and characterization of angiotensin I-converting enzyme inhibitory peptides derived from bonito bowels, Biosci. Biotech. Biochem., 1993, 57: 1743-1744 and Fujita, H. et al., Antihypertensive effect of thermolysin digest of dried bonito in spontaneously hypertensive rat, Clin. Exp. Pharmacol. Physiol. Suppl., 1995, 22: S304-S305), and fermented foods, such as sake and wine residue (Saito, Y. et al., Structure and activity of angiotensin I converting enzyme inhibitory peptides from sake and sake lees, Biosci. Biotechnol. Biochem., 1994, 58: 1767-1771), soy sauce (Kinoshita, E. et al., Purification and identification of an angiotensin I-converting enzyme inhibitor from soy sauce, Biosci. Biotechnol. Biochem., 1993, 57: 1107-1110), cheese (Okamoto, A. et al., Angiotensin I converting enzyme inhibitory activities of various fermented foods, Biosci. Biotechnol. Biochem., 1995, 59: 1147-1149) and sour milk (Masuda, O. et al., Antihypertensive peptides are present in aorta after oral administration of sour milk containing these peptides to spontaneously hypertensive rats, J. Nutr., 1996, 126: 3063-3068).

JP7289281 (A) discloses that the fermented product of soy bean with *Aspergillus niger* has ACE inhibitory activity. JP4299991 (A) discloses that a peptide product obtained by hydrolyzing soy bean with bromelain (a proteinase) has ACE inhibitory activity. JP2002053595 (A) discloses that the peptides from a soy bean hydrolysate can inhibit ACE activity. JP6298794 (A) discloses a process for the preparation of ACEI from the proteins of animal and plant sources, such as fish meats, pork and chicken. The hydrolysate is subjected to centrifugation, filtration, concentration and resin absorption to obtain the peptides with ACE inhibitory activity. JP5331192 (A) discloses that dried katsuobushi can be hydrolyzed by thermolysin to produce a peptide with ACE inhibitory activity. JP4264098 (A) discloses the preparation of a peptide with ACE inhibitory activity from chicken meat containing no fat. U.S. Pat. No. 5,854,029 discloses a process for the preparation of a dipeptide exhibiting ACE inhibitory activity. U.S. Pat. No. 6,767,990 B1 discloses peptides isolated from the hydrolysate of chicken residue. US 20120107409 A1 discloses a method for preparing a fish skin fermentation product which can inhibit the activity of tyrosinase, inhibit the activity of angiotensin-converting enzyme and/or improve the survival of fibroblasts.

A need still exists in the art for ACE inhibitors, particularly peptides from natural sources, which are more safe than the chemically synthesized compounds.

SUMMARY OF THE INVENTION

The present invention relates to novel peptides of Tyr-Tyr, Thr-Phe, Thr-Ser-Phe, Asn-Asp-Glu-Gly (SEQ ID NO: 1), Phe-Asp-Thr, Phe-Val-Asn-His-Phe (SEQ ID NO: 2), Gly-Leu-Phe, Val-Val-Asn, Thr-Tyr-Ala, Asn-Ser-Leu, Leu-Phe, Gly-Asn-Phe, Lys-Lys, Val-Gly-Gly-Ser (SEQ ID NO: 3), and Trp-Asn that inhibit ACE.

In another embodiment, the present invention relates to a composition comprising an effective amount of one or more peptides selected from Tyr-Tyr, Thr-Phe, Thr-Ser-Phe, Asn-Asp-Glu-Gly (SEQ ID NO: 1), Phe-Asp-Thr, Phe-Val-Asn-His-Phe (SEQ ID NO: 2), Gly-Leu-Phe, Val-Val-Asn, Thr-Tyr-Ala, Asn-Ser-Leu, Leu-Phe, Gly-Asn-Phe, Lys-Lys, Val-Gly-Gly-Ser (SEQ ID NO: 3), Trp-Asn, Phe-Val, and Leu-Leu and one or more carriers, diluents, solvents, colorants, anti-oxidants, inert materials and/or additives.

In a further embodiment, the present invention provides a method for preventing and treating one or more syndromes associated with angiotensin converting enzyme in a subject in need thereof, comprising administering to the subject the composition of the invention or an effective amount of one or more peptides selected from Tyr-Tyr, Thr-Phe, Thr-Ser-Phe, Asn-Asp-Glu-Gly (SEQ ID NO: 1), Phe-Asp-Thr, Phe-Val- Asn-His-Phe (SEQ ID NO: 2), Gly-Leu-Phe, Val-Val-Asn, Thr-Tyr-Ala, Asn-Ser-Leu, Leu-Phe, Gly-Asn-Phe, Lys-Lys, Val-Gly-Gly-Ser (SEQ ID NO: 3), Trp-Asn, Phe-Val, and Leu-Leu.

DETAILED DESCRIPTION OF THE INVENTION

The invention provides isolated novel peptides having the following sequences:

```
Tyr-Tyr;

Thr-Phe;

Thr-Ser-Phe;
                                        (SEQ ID NO: 1)
Asn-Asp-Glu-Gly;

Phe-Asp-Thr;
                                        (SEQ ID NO: 2)
Phe-Val-Asn-His-Phe;

Gly-Leu-Phe;

Val-Val-Asn;

Thr-Tyr-Ala;

Asn-Ser-Leu;

Leu-Phe;

Gly-Asn-Phe;

Lys-Lys;
                                        (SEQ ID NO: 3)
Val-Gly-Gly-Ser;
and Trp-Asn.
```

These peptides can be isolated and purified from the hydrolysates of natural substances (such as animal (e.g., fish or chicken) and plant (e.g., soy bean) proteins). For example, the proteins can be obtained by the methods disclosed in U.S. Pat. No. 6,767,990 B1, U.S. Pat. No. 8,063,017 B2 and US 20120107409 A1, the contents of which are incorporated by reference.

The peptides of the invention with ACE inhibitory activity can also be prepared by known chemical synthesis. For example, the azide method, the acid chloride method, the acid anhydride method, the mixed acid anhydride method, the DCC method, the active ester method, the carboimidazol method, the oxidation-reduction method, the DCC-active method (see, for example, Schroder & Luhke, The Peptide, Vol. 1 (1996), Academic Press, New York, USA; or Izumiya et al., Peptide Synthesis, Maruzen Co., Ltd. (1975), the contents of which are incorporated by reference). These peptide synthesis methods can be performed in either solid phase or liquid phase synthesis. The amino acids having a side chain functional group such as tyrosine and threonine are preferably protected in their side chain functional groups with known protective groups such as a benzyloxycarbonyl group, t-butoxycarbonyl group or benzyl group, etc. The protective groups can be removed by any known methods.

Alternatively, according to the amino acid sequences, they can also be prepared by cloning the nucleotide sequences corresponding to the amino acid sequences of the peptides into suitable vectors and expressed in suitable host cells, plants or animals.

According to the invention, the term "isolated" or "isolation" means that the material is removed from its original environment (e.g., the natural environment if it is naturally existing). The term "isolated" does not necessarily reflect the extent to which the material has been purified by removing all other substances (e.g., impurities).

In a further embodiment of the invention, a composition comprising an effective amount of one or more peptides selected from Tyr-Tyr, Thr-Phe, Thr-Ser-Phe, Asn-Asp-Glu-Gly (SEQ ID NO: 1), Phe-Asp-Thr, Phe-Val-Asn-His-Phe (SEQ ID NO: 2), Gly-Leu-Phe, Val-Val-Asn, Thr-Tyr-Ala, Asn-Ser-Leu, Leu-Phe, Gly-Asn-Phe, Lys-Lys, Val-Gly-Gly-Ser (SEQ ID NO: 3), Trp-Asn, Phe-Val, and Leu-Leu is provided. In another embodiment of the invention, the composition comprises an effective amount of one or more peptides selected from Tyr-Tyr, Thr-Phe, Thr-Ser-Phe, Asn-Asp-Glu-Gly (SEQ ID NO: 1), Phe-Asp-Thr, Phe-Val-Asn-His-Phe (SEQ ID NO: 2), Gly-Leu-Phe, Val-Val-Asn, Thr-Tyr-Ala, Asn-Ser-Leu, Leu-Phe, Gly-Asn-Phe, Lys-Lys, Val-Gly-Gly-Ser (SEQ ID NO: 3), Trp-Asn, Phe-Val, and Leu-Leu, provided that Phe-Val and Leu-Leu are not simultaneously present. The composition of the invention is a pharmaceutical composition or a food composition. The pharmaceutical composition or food composition can be prepared in a conventional manner by mixing the peptide product with one or more conventional carriers, diluents, solvents, colorants, anti-oxidants, inert materials and/or additives to formulate the composition in the form of tablets, capsules, powder, pellets, concentrates, beverages, nutraceuticals, food additives or feeds.

According to the invention, the term "effective amount" of an active ingredient as provided herein means a sufficient amount of the ingredient to provide the desired inhibition of the activity of ACE. The exact amount required may vary from subject to subject, depending on the disease state, physical conditions, age, sex, species and weight of the subject, the specific identity and formulation of the composition, etc. Thus, it is not possible to specify an exact "effective amount." However, an appropriate effective amount can be determined by one of ordinary skill in the art using only routine experimentation.

In a further embodiment of the invention, a method is provided for preventing or treating one or more syndromes associated with angiotensin converting enzyme in a subject in need thereof, which comprises administering to the subject the composition or an effective amount of one or more peptides selected from Tyr-Tyr, Thr-Phe, Thr-Ser-Phe, Asn-Asp-Glu-Gly (SEQ ID NO: 1), Phe-Asp-Thr, Phe-Val-Asn-His-Phe (SEQ ID NO: 2), Gly-Leu-Phe, Val-Val-Asn, Thr-Tyr-Ala, Asn-Ser-Leu, Leu-Phe, Gly-Asn-Phe, Lys-Lys, Val-Gly-Gly-Ser (SEQ ID NO: 3), Trp-Asn, Phe-Val, and Leu-Leu.

According to the invention, the term "preventing" or "prevention" represents that use in relation to a condition includes administering, prior to onset of the condition, an agent to reduce the frequency or severity of or delay the onset of symptoms of a medical condition in a subject relative to a subject which does not receive the agent.

According to the invention, the term "treating" or "treatment" represents reversing, alleviating, inhibiting the progress of, or improving the disorder or condition to which such term applies, or one or more symptoms of such disorder or condition.

According to the invention, the term "subject" represents any animal, preferably a mammal, and more preferably a human. Examples of subjects include humans, non-human primates, rodents, guinea pigs, rabbits, sheep, pigs, goats, cows, horses, dogs and cats.

Artisans skilled in this field know that ACE is associated with syndromes such as cardiovascular complications and hypertrophy and/or hyperplasia of adipocytes. Therefore, the peptides and composition of the invention have the ability to treat or prevent arterial hypertension, systolic hypertension, peripheral vascular disease, atherosclerosis, restenosis, heart failure, cardiac insufficiency, thrombosis and any thromboembolic events, angina pectoris, cerebral vascular accidents, coronary artery disease, myocardial infarction, vascular remodeling, and the combination thereof, and/or to reduce intraperitoneal fat and/or subcutaneous fat.

The following examples are for explication of the feasibility of the invention to substantiate the technical contents of the invention but not to limit the scope of the invention. Any variations and modifications of the invention by persons skilled in the art on the basis of the teaching of the prior art are within the scope of the invention.

EXAMPLES

Example 1

Preparation of Soybean Residues 25 kg of defatted soybean powder (purchased from Central Union Oil Corp.) was mixed with an amount of water half the weight of the defatted soybean powder; the mixture was steamed at 100° C. for 45 minutes and then cooled to 45° C. 4.2 g of koji (purchased from Higuchi Matsunosuke Shouten Co Ltd. Japan) containing *Aspergillus sojae* was added to and mixed with the mixture, and the mixture was fermented at 27° C. with 95% relative humidity for 48 hours. After fermentation, an amount of water 3 times the weight of the fermented mixture was added to the mixture and the mixture was hydrolyzed at 45° C. for 8 hours. The hydrolysate was pumped through a filter cloth to separate the fluid portion from the solid soybean residue.

Example 2

Preparation of Peptides with ACE Inhibition Activity

Soybean residue prepared by the process of Example 1 was mixed with 1 L of water and the pH of the mixture was adjusted to 2.0. 0.5 g of pepsin was added to the mixture, which was allowed to be hydrolyzed at 37° C. for 2 hours to obtain a hydrolysate. The pH of the hydrolysate was adjusted to 7.2 by using $NaHCO_3$. 0.5 g of trypsin and 0.5 g of chymotrypsin were then added to the hydrolysate, which was allowed to be further hydrolyzed at 37° C. for 2.5 hours to obtain a further hydrolysate. The further hydrolysate was heated in a boiling water bath for 15 minutes to inactive the enzymes. After cooling, the further hydrolysate was centrifuged at 10,000 rpm for 10 minutes to separate the supernatant from the solid pellet. The supernatant was then lyophilized to obtain a dried powder of 43 g, in which the amount of protein was 24.5%.

The dried powder was dissolved in water to prepare a 1% (w/v) water solution. The solution was filtered through a film with a pore size of 0.45 μm. The filtrate was subjected to high performance liquid chromatography (HPLC). The conditions used in the size exclusion column were as follows:

System: AKTA purifier
Elution column: Superdex Peptide HR 10/30
Sample amount: 500 μL
Elution fluid: 5% alcohol in pure water
Flow rate: 0.25 mL/min
Detector: 214 nm.

Every 20 minutes, a 5-mL sample eluted from the column was collected, and a total of 7 eluted fractions were collected. The above HPLC process was repeated 60 times, and all the collected corresponding fractions were respectively mixed and lyophilized to obtain 7 dried powder samples. Each dried powder sample was dissolved in water to prepare a 1% (w/v) water solution. The ACE inhibition activities of all the water solutions were respectively determined by the protocol disclosed by Vermeirssen, V. et al. (Optimisation and validation of an angiotensin-converting enzyme inhibition assay for the screening of bioactive peptides, J. Biochem. Biophys. Methods, 2002, 51: 75-87). As shown in Table 1, among all the solutions, the ACE inhibition activities of the solutions of Fractions 3, 4 and 5 were stronger, and the solution of Fraction 3 had the strongest activity.

TABLE 1

|  | Protein concentration (mg/mL) | ACE $IC_{50}$ (mg/mL) |
| --- | --- | --- |
| Fraction 1 | 6.61 | — |
| Fraction 2 | 21.33 | 0.871 |
| Fraction 3 | 17.10 | 0.014 |
| Fraction 4 | 3.80 | 0.018 |
| Fraction 5 | 0.75 | 0.025 |
| Fraction 6 | 0.69 | 0.102 |
| Fraction 7 | 0.53 | 0.593 |

The solution of the $3^{rd}$ fraction was further eluted by Sephasil Peptide RP-18 column under the following conditions:

System: AKTA purifier
Elution column: Sephasil Peptide RP-18 (5 μm) ST 4.6/250
Sample amount 100 μL
Elution fluid A: $H_2O$ containing 0.1% trifluoroacetic acid
Elution fluid B: MeOH containing 0.1% trifluoroacetic acid
Gradient: 0% B for 5 min
0-100% B for 30 min
100% B for 10 min
Flow rate: 1 mL/min
Detector: 214 nm.

Every 5 minutes, a sample eluted from the column was collected, and a total of 6 eluted fractions were collected. The above elution was repeated 250 times. All the 6 eluted fractions were respectively mixed and lyophilized to obtain 6 dried powder samples. Each dried powder sample was dissolved in 1 mL water to prepare a water solution. The ACE inhibition activity of the solution of each fraction was measured. The results show that Fractions 3-2, 3-3 and 3-4 have a better inhibition activity and that Fraction 3-4 has the best inhibition activity (see Table 2 below).

TABLE 2

|  | Protein concentration (mg/mL) | ACE $IC_{50}$ (mg/mL) |
| --- | --- | --- |
| Fraction 3-1 | 1.86 | 1.269 |
| Fraction 3-2 | 8.88 | 0.072 |

TABLE 2-continued

|  | Protein concentration (mg/mL) | ACE IC$_{50}$ (mg/mL) |
|---|---|---|
| Fraction 3-3 | 5.77 | 0.069 |
| Fraction 3-4 | 4.97 | 0.051 |
| Fraction 3-5 | 1.32 | 0.112 |
| Fraction 3-6 | 0.04 | — |

The materials at m/z 100-800 in Fraction 3-4 were determined by mass spectrometer after being eluted by Luna C18 (2) column under the following conditions:
Pump: Waters 600
Elution column: Luna C18(2) 150*2 mm, 3μ
Sample amount: 20 μL
Elution fluid A: H$_2$O containing 0.1% formic acid
Elution fluid B: acetonitrile containing 0.1% formic acid
Gradient: 5% B for 1 min
5-95% B for 24 min
95% B for 10 min
Flow rate: 0.2 mL/min
Detector: Quattro LC MS/MS.

Seventeen peptides were identified. The ACE inhibition activities of the 17 peptides were measured by the method disclosed in Pripp, A. H. et al. (Quantitative structure-activity relationship modeling of ACE-inhibitory peptides derived from milk proteins, Eur. Food Res. Technol., 2004, 219: 579-583). According to the results shown in Table 3 below, all the 17 peptides effectively inhibit the activity of ACE, and thus can be used as ACE inhibitors.

TABLE 3

| Peptides | SEQ ID NOs | MW | Retention time (min) | log IC$_{50}$ | IC$_{50}$ (μmol/L) | IC$_{50}$ (mg/mL) |
|---|---|---|---|---|---|---|
| YY |  | 344 | 24.61 | 2.41 | 256.92 | 0.088 |
| TF |  | 266 | 5.46 | 1.66 | 46.23 | 0.012 |
| TSF |  | 353 | 8.61 | 1.19 | 15.64 | 0.006 |
| NDEG | 1 | 433 | 24.88 | 2.89 | 768.42 | 0.333 |
| PDT |  | 331 | 2.86 | 2.44 | 272.33 | 0.090 |
| FVNHF | 2 | 663 | 4.04 | 1.71 | 51.10 | 0.034 |
| GLF |  | 335 | 25.2 | 1.92 | 83.04 | 0.028 |
| VVN |  | 330 | 7.24 | 1.89 | 77.05 | 0.025 |
| TYA |  | 353 | 6.88 | 2.72 | 526.14 | 0.186 |
| NSL |  | 332 | 17.86 | 1.81 | 64.86 | 0.022 |
| LF |  | 278 | 7.12 | 1.92 | 83.04 | 0.023 |
| GNF |  | 336 | 25.39 | 1.43 | 26.85 | 0.009 |
| KK |  | 274 | 3.78 | 2.96 | 921.30 | 0.252 |
| VGGS | 3 | 318 | 4.82 | 1.55 | 35.46 | 0.011 |
| WN |  | 318 | 25.56 | 2.57 | 367.71 | 0.117 |
| FV |  | 264 | 5.33 | 2.99 | 978.59 | 0.258 |
| LL |  | 244 | 5.58 | 2.54 | 344.51 | 0.084 |

What is claimed is:

1. An isolated peptide of Phe-Val-Asn-His-Phe (SEQ ID NO: 2).

2. A composition comprising an isolated peptide of Phe-Val-Asn-His-Phe (SEQ ID NO: 2) and one or more carriers, diluents, solvents, colorants, anti-oxidants, inert materials and/or additives.

3. The composition of claim 2, which is a pharmaceutical composition.

4. The composition of claim 2, which is a food composition.

5. The composition of claim 4, which is a nutraceutical or a food additive.

6. A method for inhibiting angiotensin converting enzyme in a subject, comprising administering to the subject a composition of claim 2.

7. The method of claim 6 for treating cardiovascular complications in the subject, wherein the cardiovascular complications are selected from arterial hypertension, systolic hypertension, peripheral vascular disease, atherosclerosis, restenosis, heart failure, cardiac insufficiency, thrombosis and any thromboembolic events, angina pectoris, cerebral vascular accidents, coronary artery disease, myocardial infarction, vascular remodeling, and the combination thereof.

8. The method of claim 6 for reducing hypertrophy and/or hyperplasia of adipocytes in the subject.

9. The method of claim 8 for reducing intraperitoneal fat and/or subcutaneous fat in the subject.

10. A method for inhibiting angiotensin converting enzyme in a subject, comprising administering to the subject an effective amount of an isolated peptide of Phe-Val-Asn-His-Phe (SEQ ID NO: 2).

11. The method of claim 10 for treating cardiovascular complications in the subject, wherein the cardiovascular complications are selected from arterial hypertension, systolic hypertension, peripheral vascular disease, atherosclerosis, restenosis, heart failure, cardiac insufficiency, thrombosis and any thromboembolic events, angina pectoris, cerebral vascular accidents, coronary artery disease, myocardial infarction, vascular remodeling, and the combination thereof.

12. The method of claim 10 for reducing hypertrophy and/or hyperplasia of adipocytes in the subject.

13. The method of claim 12 for reducing intraperitoneal fat and/or subcutaneous fat in the subject.

* * * * *

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Asn Asp Glu Gly
1

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Phe Val Asn His Phe
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Val Gly Gly Ser
1
```